(12) United States Patent
Christmas

(10) Patent No.: US 11,961,617 B2
(45) Date of Patent: Apr. 16, 2024

(54) PATIENT CONTROLLED INTEGRATED AND COMPREHENSIVE HEALTH RECORD MANAGEMENT SYSTEM

(71) Applicant: Crystal Christmas, Houston, TX (US)

(72) Inventor: Crystal Christmas, Houston, TX (US)

( * ) Notice: Subject to any disclaimer, the term of this patent is extended or adjusted under 35 U.S.C. 154(b) by 271 days.

(21) Appl. No.: 16/839,633

(22) Filed: Apr. 3, 2020

(65) Prior Publication Data

US 2020/0321125 A1 Oct. 8, 2020

Related U.S. Application Data

(60) Provisional application No. 62/828,731, filed on Apr. 3, 2019.

(51) Int. Cl.
*G16H 50/20* (2018.01)
*G16H 10/20* (2018.01)
(Continued)

(52) U.S. Cl.
CPC ............. *G16H 50/20* (2018.01); *G16H 10/20* (2018.01); *G16H 10/60* (2018.01); *G16H 20/00* (2018.01); *G16H 70/20* (2018.01); *G16H 70/60* (2018.01)

(58) Field of Classification Search
CPC ........ G16H 50/20; G16H 10/20; G16H 10/60; G16H 20/00; G16H 70/20; G16H 70/60;
(Continued)

(56) References Cited

U.S. PATENT DOCUMENTS

| 2012/0035959 A1 | 2/2012 | Berdia | |
| 2012/0084092 A1* | 4/2012 | Kozuch | G16H 10/20 |
| | | | 705/2 |

(Continued)

FOREIGN PATENT DOCUMENTS

WO WO-2014105752 A1 * 7/2014 ............. G16H 10/20

OTHER PUBLICATIONS

El aboudi et al., "Big Data Management for Healthcare Systems: Architecture, Requirements, and Implementation", Jun. 21, 2018, Advances in Bioinformatics (Year: 2018).*

*Primary Examiner* — Jason B Dunham
*Assistant Examiner* — Amanda R. Covington
(74) *Attorney, Agent, or Firm* — Thompson Patent Law Offices PC

(57) ABSTRACT

Apparatus and associated methods relate to a health record management system having a processing engine configured to collect one or more health records associated with a patient from one or more healthcare providers and collect one or more personal observations identified by the patient, and integrate those collected information to form a comprehensively integrated health record associated with the patient. In an illustrative example, the patient may selectively share all or part of the comprehensively integrated health record with one or more persons or assigned healthcare providers. Various embodiments may enable, for example, the patient and the assigned healthcare providers to have a better understanding on the health condition of the patient and/or predict probable outcomes of various courses of treatment based on collective data of other similar cases such that the patient and the assigned healthcare providers may observe more accurate and comprehensive information on the individual patient and/or predicted outcomes to prescribe a more effective treatment plan and/or diagnose a condition at an earlier stage.

25 Claims, 7 Drawing Sheets

(51) Int. Cl.
*G16H 10/60* (2018.01)
*G16H 20/00* (2018.01)
*G16H 70/20* (2018.01)
*G16H 70/60* (2018.01)

(58) Field of Classification Search
CPC ......... G16H 50/30; G06F 19/30; G06F 19/32; G06F 19/34; G06Q 50/22; G06Q 50/24
See application file for complete search history.

(56) References Cited

U.S. PATENT DOCUMENTS

| | | | |
|---|---|---|---|
| 2019/0189253 A1* | 6/2019 | Kartoun | G16H 20/00 |
| 2019/0244683 A1* | 8/2019 | Francois | G16H 10/60 |
| 2020/0005900 A1* | 1/2020 | Cha | G16B 50/00 |

* cited by examiner

PATIENT CONTROLLED INTEGRATED AND COMPREHENSIVE HEALTH RECORD MANAGEMENT SYSTEM

CROSS-REFERENCE TO RELATED APPLICATIONS

This application claims the benefit of U.S. Provisional Application Ser. No. 62/828,731, titled "Patient progress System and Method of Use," filed by Crystal Christmas, on Apr. 3, 2019.

This application incorporates the entire contents of the foregoing application(s) herein by reference.

This application may contain related subject matter and/or have a common inventor with U.S. application Ser. No. 16/840,181, titled "Patient Progress System and Method of Use," filed Apr. 3, 2020 by Crystal Christmas.

TECHNICAL FIELD

Various embodiments relate generally to a patient controlled health record management system and treatment system.

BACKGROUND

Healthcare systems are well known in the art and are effective means to improve or remedy the situation of a person relating to their wellbeing. For example, patients visit medical professionals such as doctors or therapists to receive treatment from illness or injury. Records of these visits and treatments are commonly retained by the doctors for their reference. In cases of chronic or complex illness or injury, treatment may be prolonged and involved. In these cases, several doctors or other professionals collaborate on the treatment. This creates the possibility of confusion as each professional keeps and maintains separate records. Additionally, the data or records collected are subjective to the person recording the data.

Accordingly, although great strides have been made in the area of healthcare systems, many shortcomings remain.

SUMMARY

Apparatus and associated methods relate to a health record management system having a processing engine configured to collect one or more health records associated with a patient from one or more healthcare providers and one or more personal observations or symptoms identified by the patient, and integrate those collected information to form a comprehensively integrated health record associated with the patient. In an illustrative example, the patient may selectively share all or part of the comprehensively integrated health record with one or more persons and/or assigned healthcare providers or entities (e.g., an insurance company verifying disability). Various embodiments may enable, for example, the patient and the assigned doctors to have a better understanding on the health condition of the patient and/or predict probable outcomes of various courses of treatment based on collective data of other similar cases such that the patient and the assigned doctors may utilize more accurate and comprehensive information on the individual patient and/or predicted outcomes to prescribe a more effective treatment plan and/or diagnose a condition at an earlier stage.

Apparatus and associated methods also relate to a treatment management system having a machine learning engine trained to (a) dynamically predict the patient's future health condition in response to the dynamically updated integrated health record associated with the patient, and (b) generate a corresponding treatment plan based on the current and/or the predicted future health condition. In an illustrative example, the machine learning engine may be trained by open-source data, and/or other patients' integrated health records, the corresponding health conditions of those patients, and the corresponding treatment plans. Various embodiments may enable, for example, the patient and the healthcare provider to take precautions against any newly discovered risks and prescribe a more effective treatment plan. Various embodiments may also provide prediction on which treatment or protocol might be best for a patient as well as the patient's future health condition.

Various embodiments may achieve one or more advantages. For example, some embodiments may advantageously provide early detection on some diseases (e.g., chronic problem detection). Some embodiments may provide a dual-party system that both the patient and related one or more healthcare providers may input data into the system through, for example, computer or mobile device. In some embodiments, the healthcare provider may be able to see a complete picture of the patient's health condition so the healthcare provider may prescribe a treatment plan that may produce better outcomes. Some embodiments may enable the healthcare provider to dynamically adjust the prescribed treatment plan in the event of earlier detection of failure through comprehensive and real-time reporting. In some embodiments, as the system may advantageously predict the patient's future health condition and because comprehensive information such as patient observations will be recorded in real time, future hospitalization may be reduced or avoided. Some embodiments may be able to provide a family health record such that the healthcare provider may have a comprehensive understanding of a newborn baby's health condition by having access to parents' comprehensive health record and family genetic history. In some embodiments, as the patient may access the system and provide inputs, the patient's integrated health record may be updated dynamically, and the system may be able to provide real-time capture to the assigned healthcare providers, other person or practitioners.

The details of various embodiments are set forth in the accompanying drawings and the description below. Other features and advantages will be apparent from the description and drawings, and from the claims.

DETAILED DESCRIPTION OF ILLUSTRATIVE EMBODIMENTS

Figure 1:
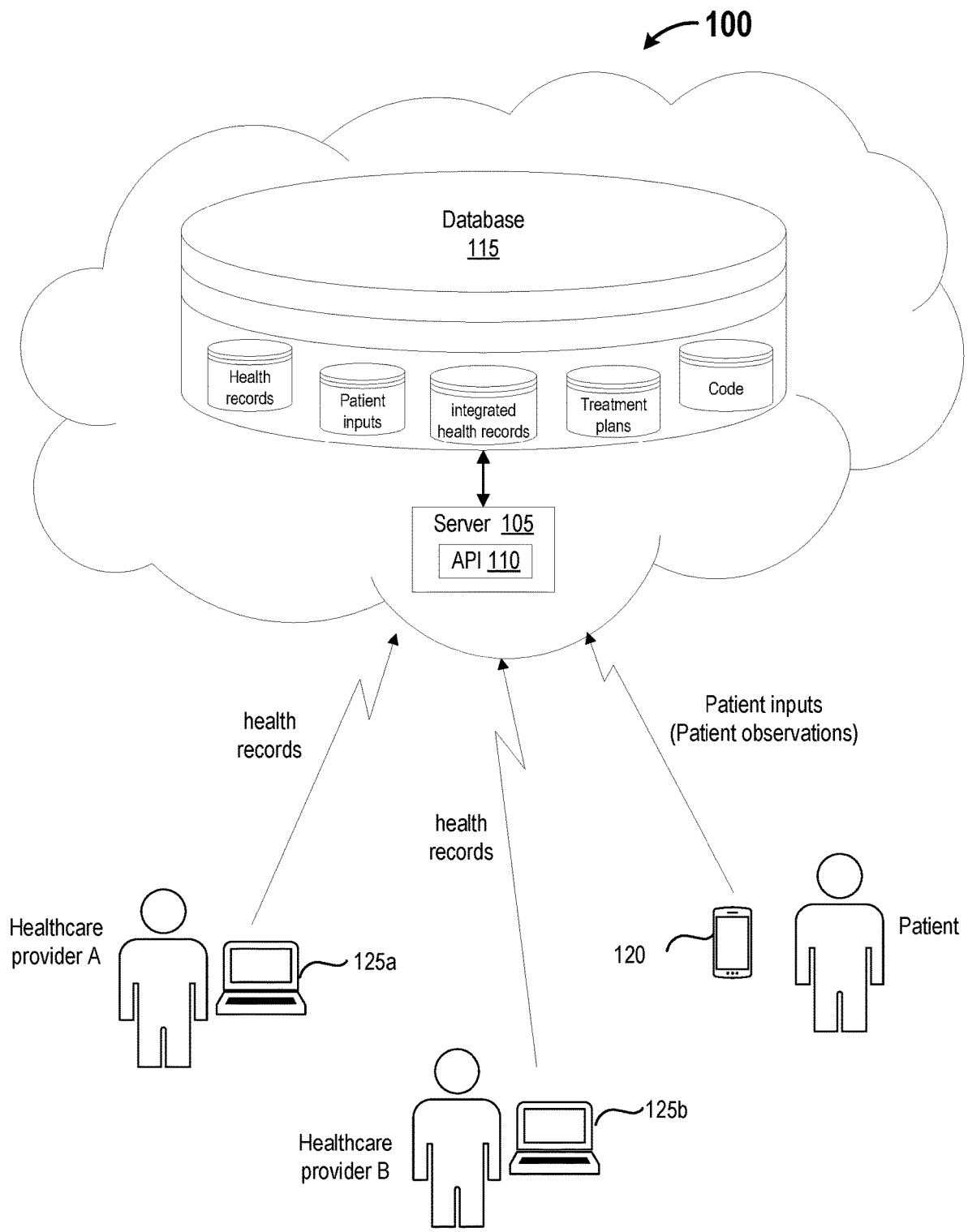
FIG. 1 depicts an exemplary health record management and treatment system employed in an illustrative use-case scenario.

FIG. 1 depicts an exemplary health record management and treatment system employed in an illustrative use-case scenario. In this depicted scenario, an exemplary health record management and treatment system (HRMTS) 100 is employed, for example, to manage patients' health conditions, perform predictions on patients' future health conditions, and provide suggested treatment or protocols to avoid predicted future health conditions. The HRMTS 100 may connect the health records associated with the same patient with collected information (e.g., symptoms as they occur in real time) from the patient himself/herself to form a comprehensively integrated health record for the patient. The health records may include electronic health records (EHR). The health records may also include, for example, dental records and other practitioner records (e.g., records kept by naturopath, nutritionist, massage therapist, counselor). By forming the comprehensively integrated health record for the patient, any authorized healthcare provider (e.g., doctors and/or physicians authorized by the patient) may be able to access the comprehensively integrated health record such that the healthcare provider may have a better understanding of the patient's health condition and advantageously provide a more appropriate suggestion and/or treatment plan.

In this depicted scenario, the HRMTS 100 includes a server 105 and a database 115 coupled to the server 105. The database 115 may contain a program of instructions that, when executed by the server 105, cause the server 105 to perform operations to generate the comprehensively integrated health record associated with the patient, share the comprehensively integrated health record, and/or predict the patient's future health condition, and recommend appropriate treatment plans or protocols accordingly. Exemplary operations that may be performed by the server 105 will be discussed in further detail with reference to FIG. 3 and FIG. 5. The database 115 may also contain collected health records, patients' inputs, the generated comprehensively integrated health records, corresponding treatment plans or protocols. In some embodiments, the database 115 may also contain open-source data. For example, practical examples of identifying different cancers and different treatments performed at different phases and corresponding outcomes.

In this depicted scenario, a patient has been taken care by a first healthcare provider (e.g., healthcare provider A) and a second healthcare provider (e.g., healthcare provider B). For example, healthcare provider A may practice related to hematology, and healthcare provider B may practice related to surgery. The patient may get one or more health records (e.g., lab test results (e.g., blood test results)) through healthcare provider A and one or more health records (e.g., CT Imaging results) through healthcare provider B. In this depicted example, the patient may also instruct the healthcare providers to upload corresponding health records to the server 105 or allow the server or an individual access to the records to populate all or part of the patient's comprehensively integrated health record. In addition, the server 105 may perform operations to communicate with the patient to get the patent's inputs. The patient's inputs may include the self-identified (e.g., physical and/or mental) symptoms (e.g., headache, cold, cough, tracked weight loss/increase depression). In some embodiments, the patent's inputs may include observations provided by a wearable device. In some embodiments, the patient's inputs may also include any other valuable information, for example, anything that may affect hormones and/or other information about the patient's lifestyle, activities and events such as exercise activities, emotional trauma—for example a death in the family, and sleeping habits. The server 105 may schedule an interview between a data collector and the patient. The interview may be recorded and then analyzed by the server 105 such that the server 105 may be able to extract predetermined information. The predetermined information may include, for example, any symptoms, any environmental changes/stimulus (e.g., divorce), and/or any family history. In some embodiments, the server 105 may also send one or more predetermined questions, or tasks to perform to the patient through an application programming interface (API) 110 to obtain information back from the patient through the personal computing devices (e.g. personal computing devices 120 or 125a 125b)

In some embodiments, the patient may send those health records (issued by same/different healthcare providers) to the server 105 through, for example, the API 110. In some embodiments, the healthcare providers and/or the patient may send requests/documents and receive responses/documents through, for example, personal computing devices (e.g., personal computing devices 120, 125a, 125b). By way of example, an embodiment of the architecture of the personal computing devices is described, with reference to [0015] of the U.S. Provisional Application Ser. No. 62/828,731, titled "Patient progress System and Method of Use," and filed by Crystal Christmas, on Apr. 3, 2019, the entire content of which is incorporated here.

By using the HRMTS 100, both the patient and the authorized healthcare providers or other persons or entities may be able to review a comprehensively integrated health record such that the healthcare providers or other persons or entities may have a better understanding of the patient's health condition, validate the presence of a health condition, and/or provide a more appropriate suggestion and/or treatment plan. In some embodiments, early detection of diseases may be also advantageously achieved. In some embodiments, verification of disability or other condition may be achieved in a more timely manner.

Figure 2A:
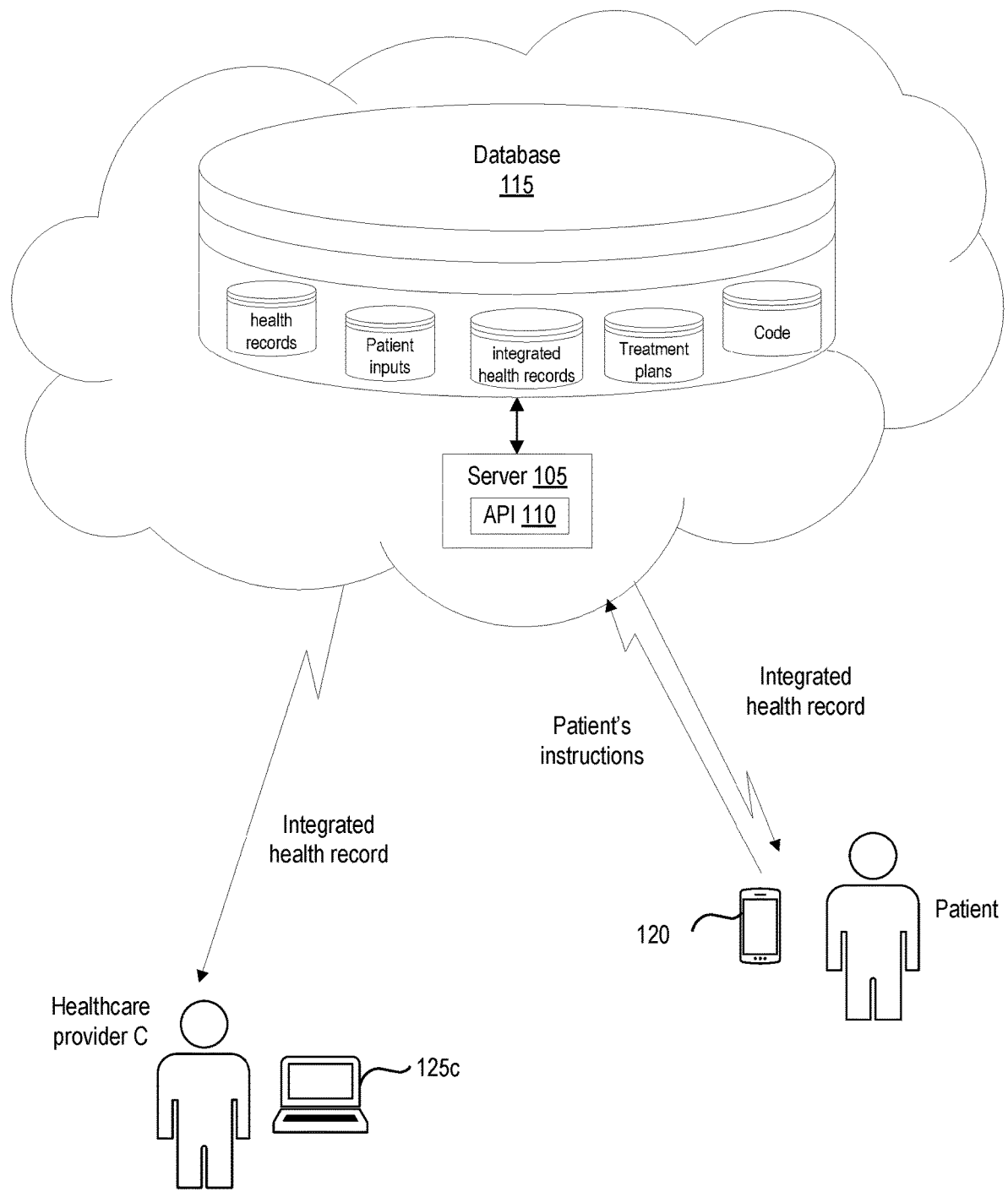
FIG. 2A depicts the exemplary health record management and treatment system employed in another illustrative use-case scenario.

FIG. 2A depicts the exemplary health record management and treatment system employed in another illustrative use-case scenario. In this depicted example, the patient may send instructions to the HRMTS 100 to request all or part of the comprehensively integrated health record. The patient may also send instructions to the HRMTS 100 to authorize the HRMTS 100 sending all or part of the comprehensively integrated health record to one or more assigned healthcare providers (e.g., doctors selected by the patient), or other persons, practitioners (e.g., caregivers, dentists, or other person who might need or use a patient's health record) or entities (e.g., government or private entities verifying disability for accommodations such as handicap license plates or disability compensation). By sharing the comprehensively integrated health record with the one or more assigned healthcare providers or other persons, practitioners or entities, the one or more assigned healthcare providers, persons, practitioners or entities may have a complete understanding of the patient's health condition and the patient, may be able to identify and/or verify a health condition faster, may also benefit from no longer needing to gather previous health records nor will the doctors, practitioners or entities need to request previous health records from other providers thus shortening the time for diagnosis and treatment of certain medical conditions and approval of disability applications or other insurance claims. In some embodiments, the patient may also choose not to share all or part of the comprehensively integrated health record through the HRMTS 100. For example, the patient may take all or part of the comprehensively integrated health record to visit the doctor or mail in for other applications as needed.

Figure 2B:
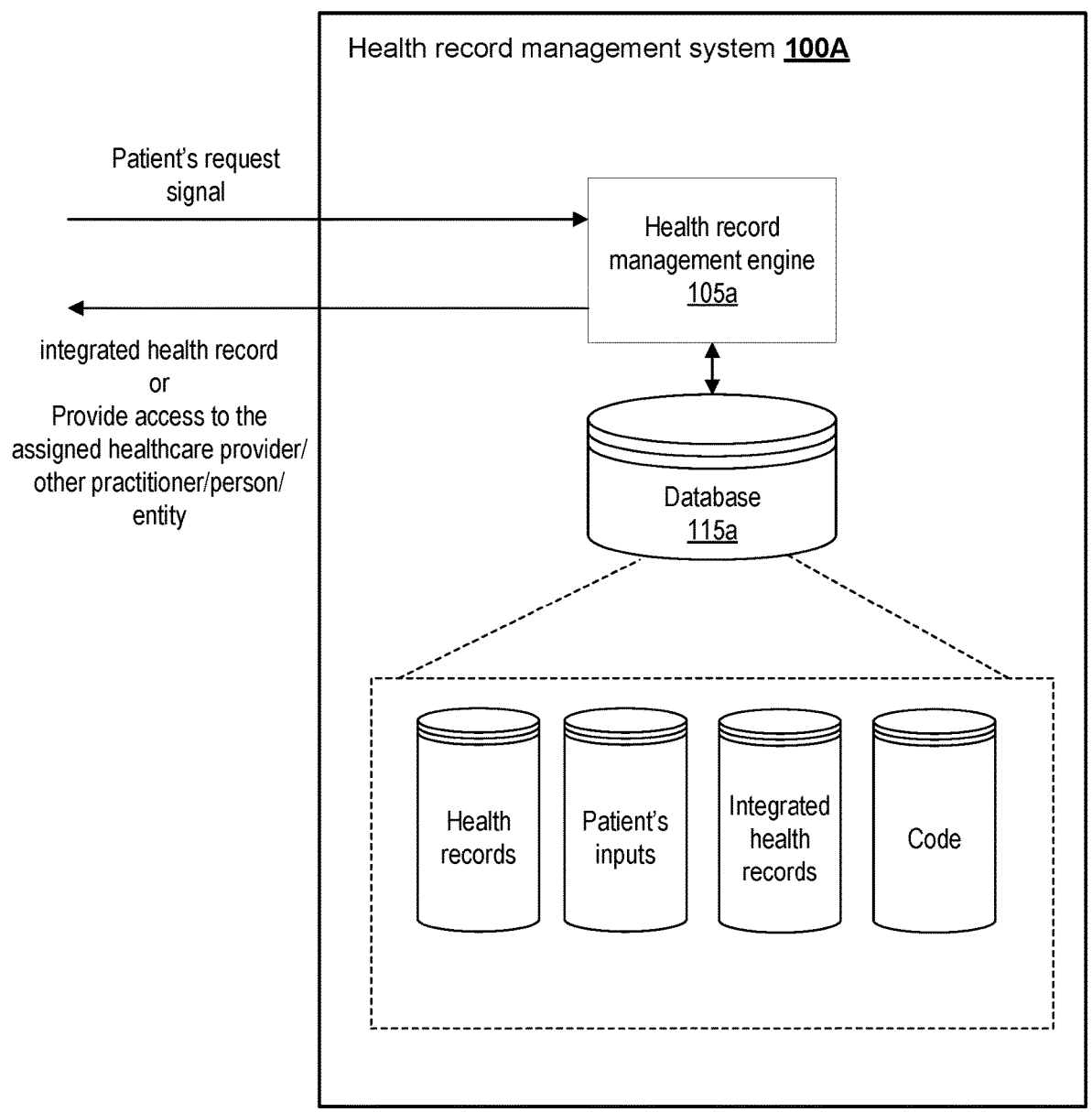
FIG. 2B depicts a block diagram of an exemplary health record management system.

FIG. 2B depicts a block diagram of an exemplary record condition management system. In this depicted example, the HRMTS 100 includes a health record management system 100A and a treatment system 100B. The block diagram of an exemplary treatment system is discussed in detail with reference to FIG. 4A.

In this depicted example, the health record management system 100A includes a health record management engine 105a and a database 115a coupled to the processing engine 105a. The database 115a may contain a program of instructions that, when executed by the processing engine 105a, cause the health record management engine 105a to perform operations to generate the comprehensively integrated health record associated with the patient and/or send all or part of the comprehensively integrated health record to the patient and/or assigned healthcare providers, other persons, practitioners, or entities. Exemplary operations that may be performed by the health record management engine 105a will be discussed in further detail with reference to FIG. 3.

Figure 3:
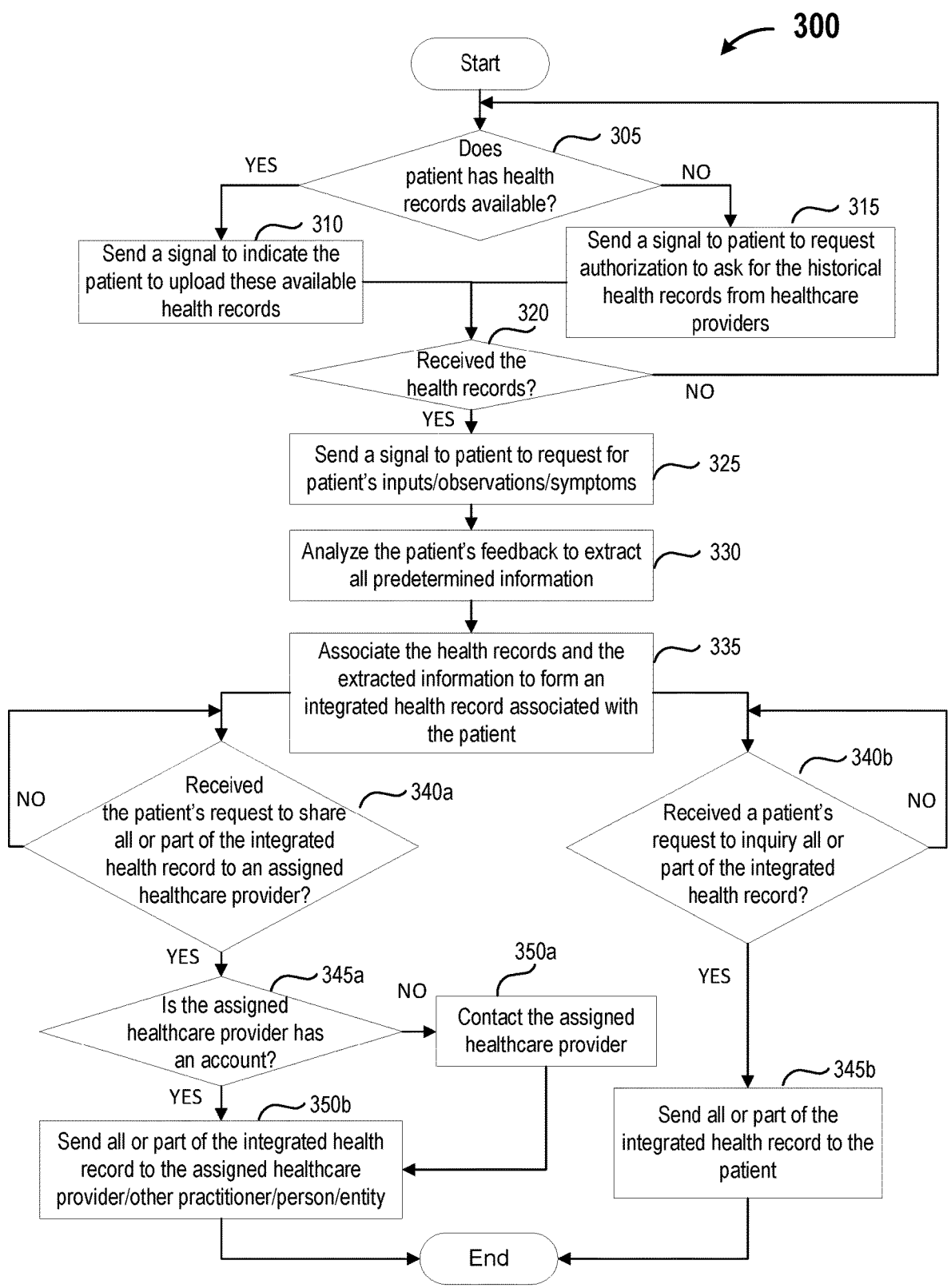
FIG. 3 depicts a flowchart of an exemplary method of generating and sharing an integrated health record.

FIG. 3 depicts a flowchart of an exemplary method of generating and sharing a comprehensively integrated health record. In response to a patient's request, a method 300 of generating and sharing the comprehensively integrated health record includes, at 305, determining (e.g., by the processing engine 105a) whether the patient has health records available. For example, when a new patient registers an account to request for a comprehensively integrated health record, in response to this request, the health record management engine 105a may be then send a corresponding signal through the API 110 to the new patient to ask whether the new patient has previous health records. If yes, then at 310, the health record management engine 105a sends a corresponding signal to the patient to indicate the patient upload the available health records. If not, then at 315, the health record management engine 105a sends a corresponding signal to the patient to request authorization to ask for health records from healthcare providers or indicate the patient to patient ask for health records from healthcare providers.

The method 300 also includes, at 320, determining whether health records associated with the patient have been received. If no, the method 300 loops back to 305. If yes, those health records are then stored in a first predetermined memory location. The method 300 includes, at 325, sending a signal to the patient to request for the patient's inputs/observations (e.g., symptoms), and storing patient's inputs/observations in a second predetermined memory location. The method 300 also includes, at 330, analyzing the patient's inputs/observations to extract predetermined information. The predetermined information may include, for example, any symptoms that were input as they occurred, any environmental changes/stimulus (e.g., divorce), any over the counter medication or supplement use and/or any family history.

In some embodiments, the processing engine may first send a signal to patient to request for patient's inputs/observations/symptoms, analyze the patient's feedback to extract all predetermined information, and then determine whether the patient has health records available.

The method 300 also includes, at 335, associating the health records and the extracted information to form the comprehensively integrated health record associated with the patient, and storing the comprehensively integrated health record in a third predetermined memory location.

In some embodiments, the method 300 may also include, at 340a, determining, by the health record management engine 105a, whether the patient sends a request to share all or part of the comprehensively integrated health record to an assigned healthcare provider, practitioner, entity, or other person. If yes, at 345a, the health record management engine 105a may then determine whether the assigned healthcare provider has an account of the HRMTS 100. If no, at 350a, the health record management engine 105a may contact the assigned healthcare provider. And if the assigned healthcare provider has an account of the HRMTS 100, then the health record management engine 105a may retrieve all or part of the comprehensively integrated health record from the third predetermined memory location and send the retrieved record to the assigned healthcare provider in response to the patient's request.

In some embodiments, the method 300 may also include, at 340b, determining, by the health record management engine 105a, whether the patient sends a request to ask for/download all or part of the comprehensively integrated health record. If yes, then the health record management engine 105a may send all or part of the comprehensively integrated health record to the patient in response to the patient's request and the patient may choose to send the integrated health record directly to the healthcare provider, practitioner, entity, or other person with or without an account through other electronic means or other delivery methods.

By generating the comprehensively integrated health record, both the patient and the authorized healthcare providers may be able to have a better understanding of the patient's health condition, and the authorized healthcare providers may provide a more appropriate suggestion and/or treatment plan. In some embodiments, early detection of diseases may be also advantageously achieved. By generating the comprehensively integrated health record that a patient can authorize for other uses, other services may be expedited such as disability benefit applications or other services or benefits that require verification of health conditions.

Figure 4A:
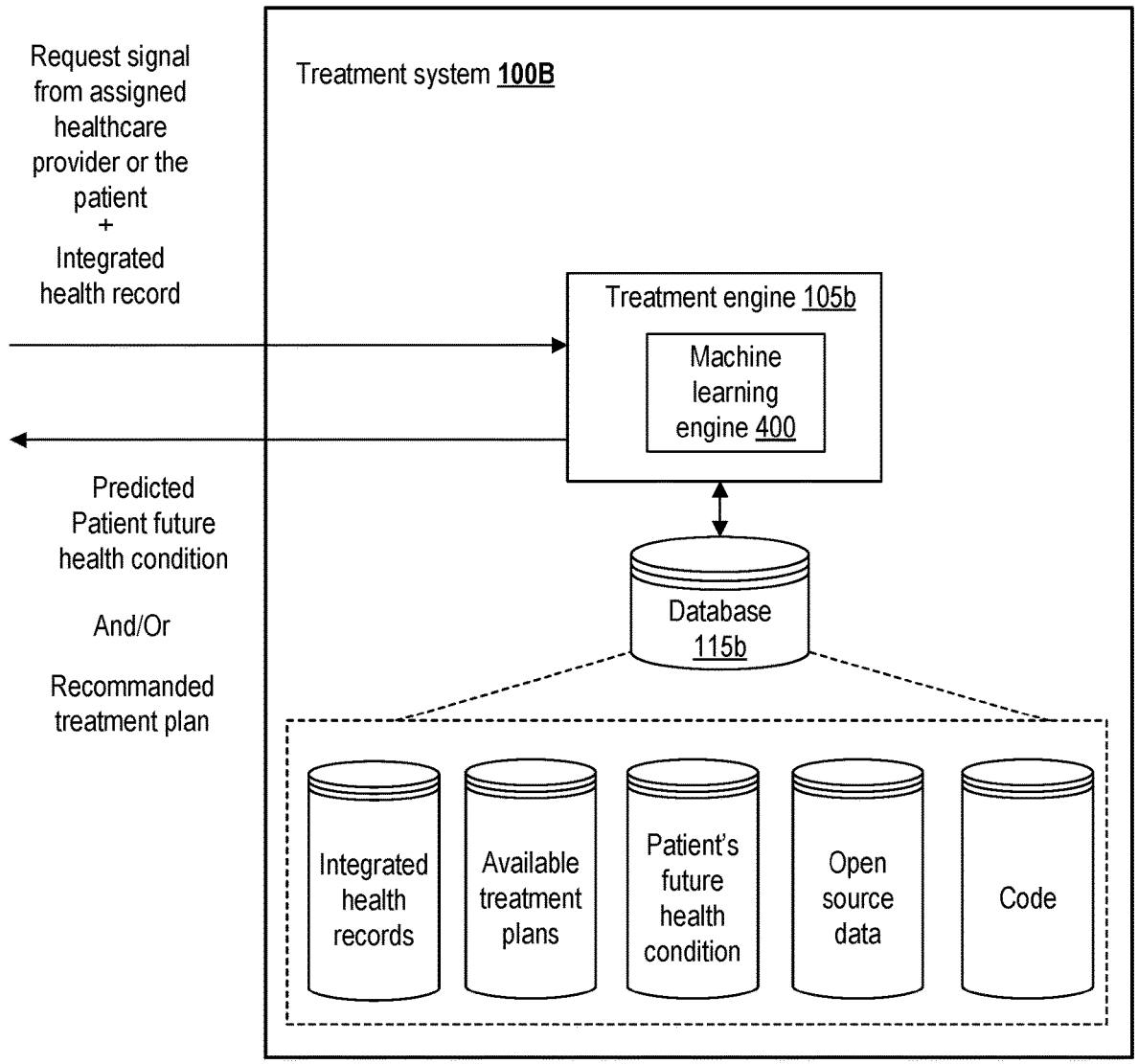
FIG. 4A depicts a block diagram of an exemplary treatment system having a machine learning engine.

FIG. 4A depicts a block diagram of an exemplary treatment system having a machine learning engine. In this depicted example, the treatment system 100B includes a treatment engine 105b and a database 115b coupled to the treatment engine 105b. The database 115b may contain a program of instructions that, when executed by the treatment engine 105b, cause the treatment engine 105b to perform operations to train a machine learning engine 400 and use the trained machine learning engine to predict the patient's future health condition and provide recommended treatment plans or protocols. In some embodiments, the machine learning engine 400 may be trained by a number of patients' comprehensively integrated health records, the corresponding health conditions, and corresponding treatment plans. In some embodiments, the machine learning engine 400 may also be trained by open data resources. The machine learning engine 400 may be used to generate the predicted future health condition of the patient and/or recommended treatment plan or protocol in response to the patient's comprehensively integrated health record. An exemplary architecture of the machine learning engine is discussed in further detail with reference to FIG. 4B. Exemplary operations that may be performed by the treatment engine 105b will be discussed in further detail with reference to FIG. 5.

Figure 4B:
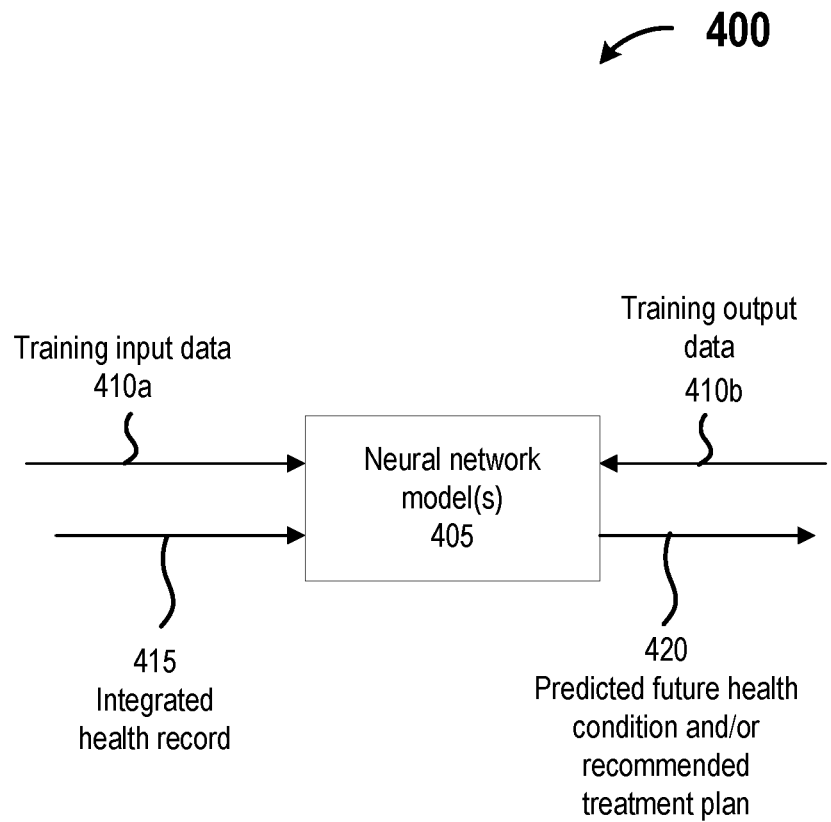
FIG. 4B depicts a block diagram of an exemplary machine learning engine.

FIG. 4B depicts a block diagram of an exemplary machine learning engine. In this depicted example, the machine learning engine 400 includes a neural network model 405. The neural network model 405 may include, for example, recurrent neural network (RNN) and/or deep neural network (DNN). Different neural network models may be selected. The number of the model layers (e.g., the hidden neurons) may also be determined based on, for example, the complexity of inventory and usage conditions. A set of training data is applied to the neural network model 405 to train the neural network model 405. The training data includes a set of training input data 410a and a set of training output data 410b. The set of training input data 410a may include a number of patients' comprehensively integrated health records (e.g., generated by the health records and patients' inputs). The set of training output data 410b may include corresponding health conditions of the patients, and corresponding treatment plans or protocols applied to the patients. In some embodiments, before training, a set of testing data (including testing input data and testing output data) may be divided from the training data. After the neural network model 405 is trained, the testing data may be applied to the trained neural network model to test the training accuracy of the model. For example, the trained neural network model may receive the testing input data and generate an output data in response to the testing input data. The generated output data may be compared with the testing output data to determine the prediction accuracy. In some embodiments, one or more neural network models may be cascaded together. The cascaded model may be trained and tested.

Figure 5:
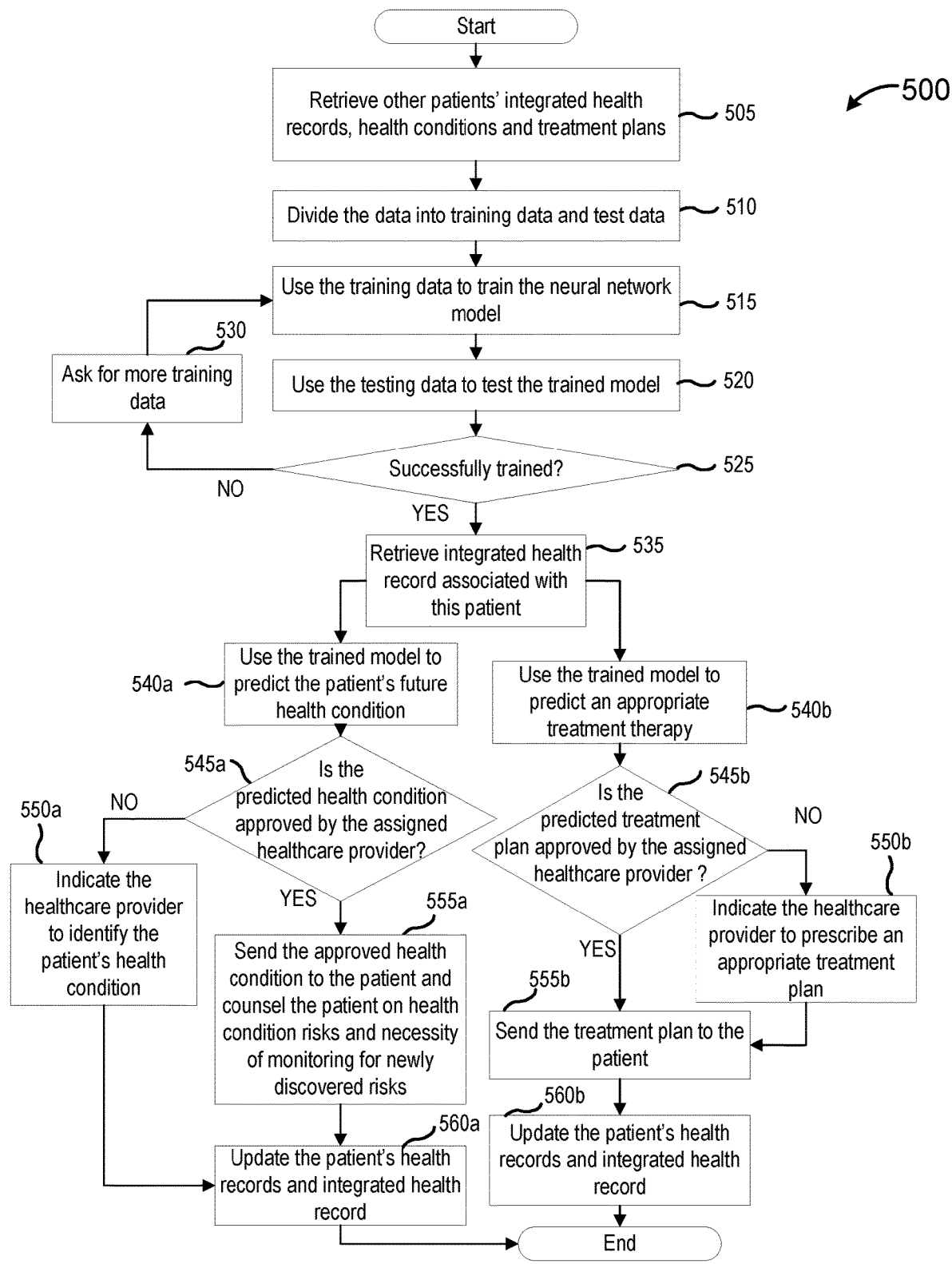
FIG. 5 depicts a flowchart of an exemplary method of training the machine learning engine to perform predictions.

FIG. 5 depicts a flowchart of an exemplary method of training the machine learning engine to perform predictions. An exemplary method 500 of training the machine learning engine and performing predictions includes, at 505, retrieving (e.g., by the treatment engine 105b) other patients' comprehensively integrated health records, health conditions, and treatment plans. The method 500 also includes, at 510, dividing the retrieved data into a first set of data used for training and a second set of data used for testing. The method 500 also includes, at 515, using the training data to train a neural network model. The method 500 also includes, at 520, applying the testing data to the trained neural network model and, at 525, determining whether the model is successfully trained. For example, if the difference between the actual output and the predicted output is within a predetermined range, then the model may be regarded as successfully trained. If the difference is not within the predetermined range, then the model may be regarded as not successfully trained. And then, at 530, the treatment engine 105b may request more training data, and the method 500 loops back to 515. If the model was successfully trained, then the method 500 also includes, at 535, retrieving this patient's comprehensively integrated health record.

The method 500 also includes, at 540a, using the trained model to predict this patient's future health condition in response to this patient's comprehensively integrated health record. The method 500 also includes, at 545a, sending the predicted future health condition to the assigned healthcare provider and determines whether the predicted future health condition is approved by the assigned healthcare provider. If the assigned healthcare provider didn't approve the predicted future health condition, at 550a, the treatment engine 105b may indicate the assigned healthcare provider to further investigate and identify the patient's health condition. If the assigned healthcare provider approved the predicted future health condition, then at 555a, the treatment engine 105b may send the approved health condition to the patient and counsel the patient on health condition risks and necessity of monitoring for newly discovered risks. The method 500 may also include, at 560a, updating the patient's health records and comprehensively integrated health records. In other embodiments, predicted future health conditions or treatment/protocol outcomes may not require an assigned healthcare provider's approval and may be used for a patient or an assigned healthcare provider to monitor the patient for development of the predicted health condition or outcome more closely and/or prevent the predicted health condition or outcome from arising.

The method 500 also includes, at 540b, using the trained model to provide a recommended treatment plan in response to this patient's comprehensively integrated health record. The method 500 also includes, at 545b, sending the recommended treatment plan to the assigned healthcare provider and determines whether the recommended treatment plan is approved by the assigned healthcare provider. If the assigned healthcare provider didn't approve the recommended treatment plan, at 550b, the treatment engine 105b may indicate the healthcare provider to prescribe an appropriate treatment plan or protocol or may recommend the patient obtain a second opinion. If the assigned healthcare provider approved the recommended treatment plan, then at 555b, the treatment engine 105b may send the approved recommended treatment plan to the patient or may recommend that the patient obtain a second opinion. The method 500 may also include, at 560b, updating the patient's health records and comprehensively integrated health records.

In one exemplary aspect, a system includes a processing engine, and, a data store coupled to the processing engine and containing a program of instructions that, when executed by the processing engine, cause the processing engine to perform operations to generate a comprehensively integrated health record associated with a patient in response to the patient's request. The operations includes (a) identifying and retrieving, by the processing engine, health records associated with the patient from the data store, (b) identifying and retrieving, by the processing engine, patient observation or patient generated information received from the patient, (c) analyzing, by the processing engine, the patient observation information and extracting predetermined data from the provided information, wherein the extracted predetermined data comprises symptoms by the patient or other patient generated data, (d) generating, by the processing engine, the comprehensively integrated health record associated with the patient in response to the retrieved health records and the extracted predetermined data.

In some embodiments, the operations may also include sending, by the processing engine, all or part of the comprehensively integrated health record to one or more predetermined healthcare providers or other persons or entities in response to a request signal from the patient. In some embodiments, the processing engine may be further configured to perform operations to predict future health condition or treatment or protocol outcomes of the patient, the operations may also include retrieving, by the processing engine, a first set of data from the data store, training on a neural network model in response to the retrieved first set of data, and, retrieving, by the processing engine, a second set of data from the data store and applying the second set of data to the trained neural network model to predict future health condition or treatment outcomes or protocol outcomes of the patient. The first set of data used to train the neural network model comprises a plurality of patients' health records, associated information provided by the plurality of patients, health conditions of the plurality of patients. The second set of data comprises the comprehensively integrated health record of the patient.

In some embodiments, the processing engine may be further configured to perform operations to provide appropriate treatment plan or protocol for the patient, the operations may also include receiving, by the processing engine, a predetermined request from the patient, retrieving, by the processing engine, the comprehensively integrated health record of the patient in response to the predetermined request, and, retrieving, by the processing engine, a corresponding treatment plan or protocol based on the comprehensively integrated health record of the patient in response to the predetermined request.

In some embodiments, the health records may include lab test results, imaging results, and/or other medical test results. In some embodiments, the health records may include electronic health records (EHR) or records manually transcribed into the system where EHR are not available. In some embodiments, the health records may include a first health record provided by a first healthcare provider and a second health record provided by a second healthcare provider. In some embodiments, the processing engine may include an application programming interface (API) configured to receive requests from the patient and send responses to the patient and predetermined healthcare providers. In some embodiments, the symptoms may include physical and mental symptoms and/or observations. In some embodiments, the extracted predetermined data may include environmental stimulus or other medical or non-medical information about the life or behavior of the patient (e.g. purchasing habits, electronic device usage, personal habits such as frequency of brushing teeth).

In another exemplary aspect, a system includes a processing engine, and, a data store coupled to the processing engine and containing a program of instructions that, when executed by the processing engine, cause the processing engine to perform operations to generate a comprehensively integrated health record associated with a patient in response to the patient's request. The operations include (a) sending, by the processing engine, a predetermined message to the patient and instructing the patient to answer the predetermined message, and report back results, (b) retrieving, by the processing engine, health records associated with the patient from the data store, (c) retrieving, by the processing engine, the patient reported results from the data store, (d) analyzing, by the processing engine, the patient reported results and extracting predetermined data from the patient reported results, the extracted predetermined data may include symptoms or observations identified by the patient, family history reported by the patient, or other patient generated data (e) integrating, by the processing engine, the health records and the extracted predetermined data to form the comprehensively integrated health record associated with the patient.

In some embodiments, the operations may also include sending, by the processing engine, all or part of the comprehensively integrated health record to one or more predetermined healthcare providers in response to the patient's request. In some embodiments, the processing engine may be further configured to perform operations to predict future health condition of the patient. In some embodiments, the operations may also include retrieving, by the processing engine, a first set of data from the data store, training on a neural network model in response to the retrieved first set of data, and, retrieving, by the processing engine, a second set of data from the data store and applying the second set of data to the trained neural network model to predict future health condition or treatment/protocol outcomes of the patient. The first set of data used to train the neural network model comprises a plurality of patients' health records, associated information provided by the plurality of patients, health conditions of the plurality of patients. The second set of data may include the comprehensively integrated health record of the patient.

In some embodiments, the processing engine may be further configured to perform operations to provide appropriate treatment plan or protocol for the patient. In some embodiments, the operations may also include retrieving, by the processing engine, the comprehensively integrated health record of the patient, and, retrieving, by the processing engine, a corresponding treatment plan or protocol based on the comprehensively integrated health record of the patient. In some embodiments, the health records may include a first health record provided by a first healthcare provider and a second health record provided by a second healthcare provider.

In another exemplary aspect, a method includes (a) retrieving, by a processing engine, health records associated with a patient, (b) retrieving, by the processing engine, information provided by the patient,(c) analyzing, by the processing engine, the information and extracting predetermined data from the provided information, wherein the extracted predetermined data comprises symptoms identified by the patient or other patient generated data, (d) integrating, by the processing engine, the health records and the extracted predetermined data to form the comprehensively integrated health record associated with the patient.

In some embodiments, the method may also include sending, by the processing engine, all or part of the comprehensively integrated health record to one or more predetermined healthcare providers in response to the patient's request. In some embodiments, the method may also include retrieving, by the processing engine, a first set of data from the data store, perform training on a neural network model in response to the retrieved first set of data, and, retrieving, by the processing engine, a second set of data from the data store and applying the second set of data to the trained neural network model to predict future health condition or treatment/protocol outcomes of the patient. The first set of data used to train the neural network model may include a plurality of patients' health records, associated information provided by the plurality of patients, health conditions of the plurality of patients. The second set of data may include the comprehensively integrated health record of the patient.

In some embodiments, the method may also include retrieving, by the processing engine, the comprehensively integrated health record of the patient, and, retrieving, by the processing engine, a corresponding treatment plan or protocol based on the integrated comprehensive health record of the patient. In some embodiments, the health records may also include a first health record provided by a first healthcare provider and a second health record provided by a second healthcare provider.

Although various embodiments have been described with reference to the figures, other embodiments are possible. For example, in some embodiments, the machine learning engine may provide a number of most probable successful treatment plans prioritized by probability of effectiveness. In some embodiments, the exemplary system 100 may also include a feature that may enable a client to create a comprehensively integrated health record for his/her whole family. For example, a newborn baby may have the same integrated record with, for example, the baby's parents and/or grandparents. The assigned healthcare provider may be able to see this family's comprehensively integrated health record if needed.

For example, some bypass circuits implementations may be controlled in response to signals from analog or digital components, which may be discrete, integrated, or a combination of each. Some embodiments may include programmed and/or programmable devices (e.g., PLAs, PLDs, ASICs, microcontroller, microprocessor), and may include one or more data stores (e.g., cell, register, block, page) that provide single or multi-level digital data storage capability, and which may be volatile and/or non-volatile. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an exemplary system 100 has been described with reference to FIG. 1, other implementations may be deployed in other industrial, scientific, medical, commercial, and/or residential applications.

Although an example of a system, which may be portable, has been described with reference to the above figures, other implementations may be deployed in other processing applications, such as desktop and networked environments. Although particular features of an architecture have been described, other features may be incorporated to improve performance. For example, caching (e.g., L1, L2, etc . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades, etc . . . ), and the like. One or more communication interfaces may be provided in support of data storage and related operations.

Some systems may be implemented as a computer system that can be used with implementations of the invention. For example, various implementations may include digital and/or analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of the invention by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits).

In some implementations, each system 100 may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. The invention may be implemented in a computer system that includes a graphical user interface and/or an Internet browser. To provide for interaction with a user, some implementations may be implemented on a computer having a display device, such as a CRT (cathode ray tube) or LCD (liquid crystal display) monitor for displaying information to the user, a keyboard, and a pointing device, such as a mouse or a trackball by which the user can provide input to the computer.

In various implementations, the system 100 may communicate using suitable communication methods, equipment, and techniques. For example, the system 100 may communicate with compatible devices (e.g., devices capable of transferring data to and/or from the system 100) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits and/or other modules. In various examples, the modules may include analog and/or digital logic, discrete components, traces and/or memory circuits fabricated on a silicon substrate including various integrated circuits (e.g., FPGAs, ASICs). In some embodiments, the module(s) may involve execution of preprogrammed instructions and/or software executed by a processor. For example, various modules may involve both hardware and software.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A system, comprising:
a processing engine;
a communication module coupled to the processing engine, comprising an application programming interface configured to provide remote access to a user device over a network, wherein the user device is configured to receive patient generated information through the application programming interface; and,
a data store coupled to the processing engine and containing a program of instructions that, when executed by the processing engine, cause the processing engine to perform operations to generate an integrated health record associated with a patient in response to the patient's request, the operations comprising:
(a) receiving patient reported information directly from the patient via the communication module from the user device, the patient generated information comprising a plurality of unprompted real-time symptom reports from the patient;
(a1) identifying and retrieving, by the processing engine, health records in a first data format associated with the patient from the data store;
(a2) retrieving, by the processing engine, family history records associated with the patient;
(b1) identifying and retrieving, by the processing engine, patient generated information received directly from the patient, the patient generated information comprising the plurality of unprompted real-time symptom reports from the patient corresponding to symptoms self-identified by the patient stored in a second data format;
(b2) identifying and retrieving, by the processing engine, environmental information temporally corresponding to the patient generated information;
(c) analyzing, by the processing engine, the patient generated information and extracting predetermined data from the retrieved information comprising information retrieved in (a1)-(b2), wherein the extracted predetermined data comprises the symptoms reported by the patient in the plurality of unprompted real-time symptom reports;
(d) generating, by the processing engine, the integrated health record associated with the patient in response to the retrieved health records, the temporally corresponding environmental information, and the extracted predetermined data, wherein the integrated health record comprises an input in a third data format suitable for a machine learning engine;
(e1) applying the machine learning engine, the machine learning engine comprising a plurality of unsupervised classification models, to the integrated health record to generate at least one predicted health condition as a function of the integrated health record, including specifically as a function of the symptoms, at least one outcome associated with the symptoms, and the temporally corresponding environmental information;
(e2) applying the machine learning engine to the integrated health record and other patients' integrated health records based on the predicted health condition, the symptoms, corresponding health conditions, corresponding treatment plans, and corresponding outcomes associated with the other patients' integrated health records to generate a plurality of potential treatment plans and corresponding predicted outcomes, and associate the plurality of potential treatment plans and the corresponding predicted outcomes with the patient;
(f) generating a result message to the user device, wherein the result message comprises the at least one predicted health condition and the symptoms, the at least one outcome, the plurality of potential treatment plans, the corresponding predicted outcomes, and the temporally corresponding environmental information; and,
(g) in response to receiving new patient information comprising at least one of: new patient generated information, and new environmental information, repeat at least (c)-(f) such that a dynamically updated results message comprising an updated plurality of potential treatment plans and corresponding predicted outcome is generated based on the new patient information,
wherein the processing engine performs operations to train the machine learning engine to generate the at least one predicted health condition and the plurality of potential treatment plans and the corresponding predicted outcomes, the operations comprise:

retrieving, by the processing engine, a first set of data from the data store;

training the machine learning engine in response to the retrieved first set of data; and, wherein the first set of data used to train the machine learning engine comprises a plurality of patients' health records including integrated health records, associated information provided by the plurality of patients, health conditions of the plurality of patients, patient generated information from the plurality of patients, treatment plans corresponding to the patient generated information, and outcomes corresponding to the treatment plans.

2. The system of claim 1, wherein the operations further comprise:

sending, by the processing engine, all or part of the integrated health record to one or more predetermined healthcare providers or other persons or entities in response to a request signal from the patient.

3. The system of claim 1, wherein the plurality of unsupervised classification models are configured as a plurality of neural network layers.

4. The system of claim 1, wherein the processing engine is further configured to perform operations to provide at least one appropriate treatment plan for the patient, the operations further comprising:

receiving, by the processing engine, a predetermined request from the patient;

retrieving, by the processing engine, the integrated health record of the patient in response to the predetermined request; and, generating, by the processing engine, a corresponding treatment plan based on the integrated health record of the patient in response to the predetermined request.

5. The system of claim 1, wherein the health records comprise at least one of medical test results or clinical findings.

6. The system of claim 1, wherein the health records comprise at least one of electronic health records (EHR) or records manually transcribed into the system.

7. The system of claim 1, wherein the health records comprise a first health record provided by a first healthcare provider and a second health record provided by a second healthcare provider.

8. The system of claim 1, wherein the processing engine comprises an application programming interface (API) configured to receive requests from the patient and send responses to the patient and predetermined healthcare providers.

9. The system of claim 1, wherein the patient generated information comprises at least one of physical symptoms, mental symptoms, or observations.

10. The system of claim 1, wherein the extracted predetermined data further comprises at least one of: environmental stimulus, and behavioral information.

11. A system, comprising:

a processing engine;

a communication module coupled to the processing engine, comprising an application programming interface configured to provide remote access to a user device over a network, wherein the user device is configured to receive patient generated information through the application programming interface; and, a data store coupled to the processing engine and containing a program of instructions that, when executed by the processing engine, cause the processing engine to perform operations to generate an integrated health record associated with a patient in response to the patient's request, the operations comprising:

(a) receiving patient reported information directly from the patient via the communication module from the user device, the patient generated information comprising a plurality of unprompted real-time symptom reports from the patient stored in a first data format;

(a2) storing the received patient reported information in the data store;

(b) retrieving, by the processing engine, health records in a second data format associated with the patient from the data store;

(c1) retrieving, by the processing engine, the patient reported information from the data store, the patient reported information comprising symptoms reported by the patient, and family history records associated with the patient;

(c2) retrieving, by the processing engine, environmental information temporally corresponding to the patient generated information;

(d) analyzing, by the processing engine, the patient reported information and extracting predetermined data from the patient reported information; and, (e) converting, by the processing engine, the health records, the temporally corresponding environmental information, and the extracted predetermined data into the integrated health record associated with the patient, wherein the integrated health record comprises an input in a third data format suitable for a machine learning engine;

(f) applying the machine learning engine to the integrated health record to generate at least one predicted health condition, a plurality of potential treatment plans and corresponding predicted outcomes as a function of the symptoms, at least one outcome associated with the symptoms, corresponding health conditions, corresponding treatment plans and corresponding outcomes associated with other patients' integrated health records, and the temporally corresponding environmental information;

(f1) associating the potential treatment plans, and the corresponding predicted outcomes with the patient;

(g) generating a result message to the user device, wherein the result message comprises the at least one predicted health condition and the symptoms, the at least one predicted outcome associated with the symptoms, the plurality of potential treatment plans, the corresponding predicted outcomes, and the temporally corresponding environmental information; and, (h) generating, in response to receiving new patient reported information comprising at least one of: the new patient reported information, and new environmental information, repeat at least (d)-(g) such that a dynamically updated results message comprising an updated plurality of potential treatment plans and the corresponding predicted outcomes is generated based on the new patient reported information, wherein the processing engine performs operations to train the machine learning engine to generate the at least one predicted future health condition of the patient, the operations further comprising:

retrieving, by the processing engine, a training set of data from the data store;

training the machine learning engine in response to the training set of data; and, wherein the training set of data used to train the machine learning engine comprises a plurality of patients' health records, associated information provided by the plurality of patients, health conditions of the plurality of patients, patient reported information from the plurality of patients, treatment plans corresponding to the patient generated information, and outcomes corresponding to the treatment plans.

12. The system of claim 11, wherein the operations further comprise:
sending, by the processing engine, all or part of the integrated health record to one or more predetermined healthcare providers in response to the patient's request.

13. The system of claim 11, wherein the machine learning engine comprises a plurality of unsupervised classification models.

14. The system of claim 11, wherein the health records comprise a first health record provided by a first healthcare provider and a second health record provided by a second healthcare provider.

15. A method, comprising:
(a1) providing remote access to a user device over a network, wherein the user device is configured to receive patient generated information of a patient through an application programming interface;
(a2) storing the received patient generated information in a first data store;
(a3) retrieving, by a processing engine from a second data store, health records in a first data format associated with the patient;
(b1) retrieving, by the processing engine, the patient generated information provided directly from the patient, wherein the patient generated information comprises a plurality of unprompted real-time symptom reports from the patient stored in a second data format;
(b2) retrieving, by the processing engine, environmental information temporally corresponding to the patient generated information, and family history records associated with the patient;
(c) analyzing, by the processing engine, the patient generated information and extracting predetermined data from the provided patient generated information, wherein the extracted predetermined data comprises symptoms identified by the patient in the plurality of unprompted real-time symptom reports;
(d) converting, by the processing engine, the health records, the temporally corresponding environmental information, the family history records, and the extracted predetermined data into an integrated health record associated with the patient, wherein the integrated health record comprises an input in a third data format suitable for a machine learning engine;
(e) applying the machine learning engine to the integrated health record to generate a predictive result comprising:
at least one predicted health condition,
a plurality of potential treatment plans and corresponding predicted outcomes, and,
an association between the plurality of potential treatment plans and the corresponding predicted outcomes with the patient, wherein:
the predictive result is generated as a function of the symptoms, corresponding health conditions, corresponding treatment plans and corresponding outcomes associated with other patients' integrated health records, at least one predicted outcome associated with the symptoms, potential treatment plans corresponding to the at least one predicted outcome, and the temporally corresponding environmental information, wherein the machine learning engine is trained on a set of data comprising a set of patient-generated data, wherein the set of patient generated data comprises a plurality of patients' health records, associated information provided by the plurality of patients, health conditions of the plurality of patients, patient reported information from the plurality of patients, historical treatment plans corresponding to the plurality of patients, and historical outcomes corresponding to the historical treatment plans;
(f) in response to the generated predictive result,
(f1) storing the predictive result in a third data store, and,
(f2) automatically generating a result message based on the predictive result and the integrated health records, wherein the result message comprising the at least one predicted health condition and the symptoms, the at least one predicted outcome, the plurality of potential treatment plans, the corresponding predicted outcomes, and the temporally corresponding environmental information; and,
(g) in response to receiving new patient information comprising at least one of: new patient generated information, and new environmental information, repeating at least (c)-(f) such that a dynamically updated result message comprising an updated plurality of potential treatment plans and corresponding predicted outcomes is generated based on the new patient information.

16. The method of claim 15, further comprising:
sending, by the processing engine, all or part of the integrated health record to one or more predetermined healthcare providers in response to a request from the patient.

17. The method of claim 15, wherein the machine learning engine comprises a plurality of unsupervised classification models.

18. The method of claim 15, further comprising:
retrieving, by the processing engine, the integrated health record of the patient; and,
retrieving, by the processing engine, a corresponding treatment plan based on the integrated health record of the patient.

19. The method of claim 15, wherein the health records comprise a first health record provided by a first healthcare provider and a second health record provided by a second healthcare provider.

20. The system of claim 1, further comprising performing training operations on the machine learning engine, wherein the training operations comprise:
(a) retrieving a set of data comprising a set of patient-generated data, wherein the set of patient-generated data comprises a plurality of patients' health records, associated information provided by the plurality of patients, and health conditions of the plurality of patients;
(b) dividing the set of patient-generated data into a training data set and a testing data set;
(c) applying the training data set to train the machine learning engine such that at least one parameter of the machine learning engine is updated;
(d) determining a training score by applying the testing data set to the trained machine learning engine to generate predicted patient health conditions, wherein the training score is generated based on an accuracy of the generated patient health conditions in comparison to the health conditions of the plurality of patients in the testing data set;

(e) if the training score is lower than a predetermined value and a maximum repetition is not reached, repeat at least (b)-(d) such that the machine learning engine is re-trained.

21. The system of claim 1, wherein the at least one predicted health condition comprises a diagnosis.

22. The system of claim 11, wherein the machine learning engine comprises a neural network model, and training the machine learning engine comprises training the neural network model.

23. The method of claim 15, wherein the health records comprise electronic health records (EHR).

24. The method of claim 15, wherein the patient generated information comprises self-identified symptoms.

25. The method of claim 15, wherein the patient generated information comprises input transmitted via a wearable device.

* * * * *